US012515001B2

(12) United States Patent
van Zanten et al.

(10) Patent No.: US 12,515,001 B2
(45) Date of Patent: Jan. 6, 2026

(54) DIAGNOSIS AND TREATMENT FOR OSA-RELATED BRUXISM

(71) Applicant: KONINKLIJKE PHILIPS N.V., Eindhoven (NL)

(72) Inventors: Joyce van Zanten, Eindhoven (NL); Joachim Johannes Kahlert, Eindhoven (NL); Pedro Miguel Ferreira dos Santos da Fonseca, Eindhoven (NL); Lutz Christian Gerhardt, Eindhoven (NL); Angela Grassi, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 726 days.

(21) Appl. No.: 17/887,880

(22) Filed: Aug. 15, 2022

(65) Prior Publication Data

US 2023/0047226 A1 Feb. 16, 2023

Related U.S. Application Data

(60) Provisional application No. 63/233,368, filed on Aug. 16, 2021.

(51) Int. Cl.
*A61M 16/00* (2006.01)
*A61M 16/06* (2006.01)
*A61M 16/08* (2006.01)

(52) U.S. Cl.
CPC ...... *A61M 16/024* (2017.08); *A61M 16/0683* (2013.01); *A61M 16/0875* (2013.01);
(Continued)

(58) Field of Classification Search
CPC ........ A61M 16/024; A61M 2205/3375; A61M 16/0683; A61M 16/0051; A61M 16/06; A61B 5/4557; A61F 2005/563
See application file for complete search history.

(56) References Cited

U.S. PATENT DOCUMENTS 8,424,527 B1 * 4/2013 Kayyali ............ A61M 16/0495 128/204.23
9,398,974 B1 7/2016 Delrio
(Continued)

OTHER PUBLICATIONS

Huynh, N. et al., "Sleep bruxism is associated to micro-arousals and an increase in cardiac sympathetic activity". J. Sleep Res. (2006) 15, 339-346.
Miettinen, T. et al., "Polysomnographic scoring of sleep bruxism events is accurate even in the absence of video recording but unreliable with EMG-only setups". Sleep and Breathing (2020) 24:893-904.
(Continued)

*Primary Examiner* — Margaret M Luarca
(74) *Attorney, Agent, or Firm* — Michael W. Haas

(57) ABSTRACT

A method and system for diagnosing, treating, and ameliorating sleep bruxism events using a positive airway pressure (PAP) system for treating obstructive sleep apnea to concurrently recognize bruxism events. At least one sensor is integrated into a therapy interface and/or headgear to detect physiological signals indicative of bruxism. In some exemplary embodiments, a loudspeaker and microphone are integrated into the interface, either near the nose or near the mouth of the patient. When integrated near the nose, the pair is used for acoustical rhinometry, and when integrated near the mouth, the pair is used for acoustical pharyngometry. In other exemplary embodiments, sound or vibration sensors are used to detect signals indicative of teeth grinding. In response to sensor detection of bruxism activity, the PAP system controller adjusts the PAP therapy settings or proposes alternative treatment modalities in order to stop or prevent bruxism events.

13 Claims, 3 Drawing Sheets

(52) U.S. Cl.
CPC ............... *A61M 2016/0027* (2013.01); *A61M 2205/3375* (2013.01)

(56) References Cited

U.S. PATENT DOCUMENTS

| | | | | |
|---|---|---|---|---|
| 2010/0206313 | A1 | 8/2010 | Peake | |
| 2012/0204874 | A1* | 8/2012 | Sofranko .......... | A61M 16/0069 128/204.23 |
| 2014/0261450 | A1 | 9/2014 | Morehead | |
| 2016/0095740 | A1* | 4/2016 | Mardirossian .... | A61M 16/0683 128/847 |
| 2018/0116863 | A1 | 5/2018 | Shah | |
| 2022/0211972 | A1* | 7/2022 | Tsuboi ...................... | A61F 5/56 |

OTHER PUBLICATIONS

Miyawaki, S. et al., "Association Between Sleep Bruxism, Swallowing-Related Laryngeal Movement, and Sleep Positions". Sleep, vol. 26, No. 4, 2003.
Martinot, J-B et al., "Bruxism Relieved Under CPAP Treatment in a Patient With OSA Syndrome". doi: https://doi.org/10.1016/j.chest.2019.07.032.

* cited by examiner

DIAGNOSIS AND TREATMENT FOR OSA-RELATED BRUXISM

CROSS-REFERENCE TO RELATED APPLICATIONS

This patent application claims the priority benefit under 35 U.S.C. § 119(e) of U.S. Provisional Application No. 63/233,368, filed on Aug. 16, 2021, the contents of which are herein incorporated by reference.

BACKGROUND OF THE INVENTION

1. Field of the Invention

The present invention pertains to systems and methods for diagnosing and treating sleep bruxism events in obstructive sleep apnea (OSA) patients, and, in particular, to adapting positive airway pressure (PAP) equipment used to treat OSA to additionally detect bruxism activity for diagnostic purposes and/or to adjust the settings of PAP therapy in order to prevent future bruxism events or stop or minimize current bruxism events.

2. Description of the Related Art

Bruxism is a condition where a patient grinds, gnashes, and/or clenches his or her teeth, and is commonly associated with airway disturbance conditions such as sleep apnea and gastric reflux. Bruxism is typically an unconscious behavior and can occur both while awake and sleeping. Common symptoms of bruxism include worn tooth structure and flattening of the teeth, increased tooth sensitivity, jaw soreness, tenderness of the facial muscles, and dull headaches. In some instances, tooth grinding may be loud enough that it can be heard by others when the patient is asleep. The prevalence of bruxism in OSA patients is about 55%.

OSA is usually caused by an obstruction of the upper airway. It is characterized by repetitive pauses in breathing during sleep and is usually associated with a reduction in blood oxygen saturation. Non-invasive ventilation and pressure support therapies involve the placement of a patient interface device including a mask component on the face of a patient. The mask component may be, without limitation, a nasal mask that covers the patient's nose, a nasal cushion having nasal prongs that are received within the patient's nares, a nasal/oral mask that covers the nose and mouth, or a full face mask that covers the patient's face. The patient interface device interfaces a ventilator or pressure/flow generating device with the airway of the patient, so that a flow of breathing gas can be delivered from the ventilator or pressure/flow generating device to the airway of the patient. It is known to maintain such devices on the face of a wearer by a headgear having one or more straps adapted to fit over/around the patient's head. Known PAP therapies include continuous positive airway pressure (CPAP), wherein a constant positive pressure is provided to the airway of the patient in order to splint open the patient's airway, and variable airway pressure such as BiPAP, wherein the pressure provided to the airway of the patient is varied with the patient's respiratory cycle.

It is unclear if bruxism is an isolated neurological disorder or if it is triggered by increased sympathetic tone due to another cause. For example, a positive association has been found between the occurrence of micro-arousals from the four minutes preceding sleep bruxism (SB) onset, and, in general, a shift in sympatho-vagal balance towards increased sympathetic activity has been found to start eight minutes preceding SB onset in moderate to severe SB subjects. During the grinding of the teeth, a higher muscle activity of the tongue and the masseter muscles can be measured by electromyography (EMG) sensors. A higher muscle tone in the upper airway will tense the palatal and pharyngeal muscles, which will consequently increase the airway patency. Higher pharyngeal muscle tone is beneficial, as it stabilizes the upper airway and protects the upper airway from a narrowing or collapse caused by negative pressure during inspiration. However, it is not known if the higher sympathetic activity and the muscle activity in the mouth has an impact on the muscle tone in the upper airway.

In addition, currently, there are no means to measure the impact on the cross-section and the pressure related modulation of the airway patency during the respiration cycle. During a polysomnogram (PSG), the masticatory muscle activity (MMA) can be measured by superficial EMG sensors; however, superficial EMG activity is insufficient to distinguish between MMA activity and other muscles activity (OMA). There is thus room for improvement in systems and methods for diagnosing and treating sleep bruxism in OSA patients.

SUMMARY OF THE INVENTION

Accordingly, it is an object of the present invention to provide, in one embodiment, a set of positive airway pressure therapy (PAP) gear for recognizing sleep bruxism events in a patient during therapy for obstructive sleep apnea. The system comprises: a patient interface structured to be coupled to an airway of the patient, headgear coupled to the patient interface and structured to secure the patient interface to a head of the patient, at least one sensor is integrated into the patient interface and the headgear, and a controller electrically and operatively coupled to the sensor(s) and configured to be electrically and operatively coupled to a pressurized air generator. The sensor(s) is configured to detect physiological signals related to bruxism events, and the controller is configured to change an output of the pressurized air generator based on the signals detected by the sensor(s).

In another embodiment, a patient during therapy for obstructive sleep apnea comprises a pressurized air generator, a patient interface structured to be coupled to an airway of the patient, a conduit coupled at a first end to an output of the pressurized air generator and coupled at a second end opposite the first end to the patient interface, headgear coupled to the patient interface and structured to secure the patient interface to a head of the patient, at least one sensor is integrated into the patient interface and the headgear, and a controller electrically and operatively coupled to the sensor(s) and to the pressurized air generator. The sensor(s) is configured to detect physiological signals related to bruxism events, and the controller is configured to decide whether to change an output of the pressurized air generator or propose alternative OSA or dental treatment modalities based on the signals detected by sensor(s).

In another embodiment, a method for recognizing sleep bruxism events and stopping said sleep bruxism events in a patient during positive airway pressure (PAP) therapy for obstructive sleep apnea comprises coupling a patient interface integrated with at least one sensor to an airway of the patient, electrically and operatively coupling a controller to the sensor(s) and electrically and operatively coupling the controller to a pressurized air generator, configuring the sensor to detect physiological signals related to bruxism events, and configuring the controller to decide whether to change an output of the pressurized air generator or propose alternative OSA or dental treatment modalities based on the signals detected by the sensor(s).

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF EXEMPLARY EMBODIMENTS

Figure 1:
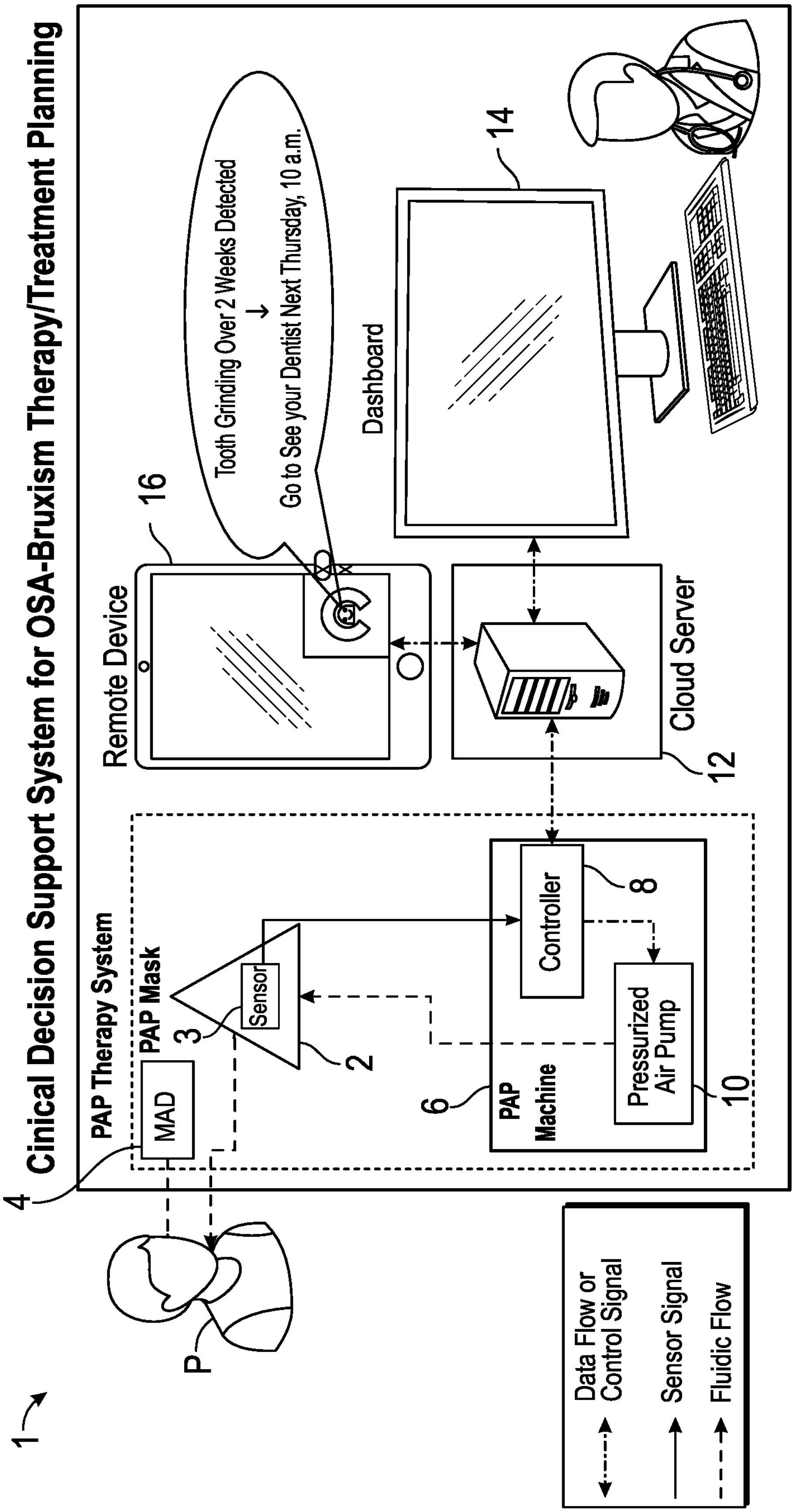
FIG. 1 is a simplified diagram of a clinical decision support system for obstructive sleep apnea (OSA) and sleep bruxism (SB) therapy and treatment planning according to an exemplary embodiment of the present invention.

As used herein, the singular form of "a", "an", and "the" include plural references unless the context clearly dictates otherwise.

As used herein, the term "controller" shall mean a number of programmable analog and/or digital devices (including an associated memory part or portion) that can store, retrieve, execute and process data (e.g., software routines and/or information used by such routines), including, without limitation, a field programmable gate array (FPGA), a complex programmable logic device (CPLD), a programmable system on a chip (PSOC), an application specific integrated circuit (ASIC), a microprocessor, a microcontroller, a programmable logic controller, or any other suitable processing device or apparatus. The memory portion can be any one or more of a variety of types of internal and/or external storage media such as, without limitation, RAM, ROM, EPROM(s), EEPROM(s), FLASH, and the like that provide a storage register, i.e., a non-transitory machine readable medium, for data and program code storage such as in the fashion of an internal storage area of a computer, and can be volatile memory or nonvolatile memory.

As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are coupled in direct contact with each other. As used herein, "fixedly coupled" or "fixed" means that two components are coupled so as to move as one while maintaining a constant orientation relative to each other. As used herein, "movably coupled" means that two components are coupled so as to allow at least one of the components to move in a manner such that the orientation of the at least one component relative to the other component may change without the components being uncoupled.

As used herein, the statement that two or more parts or components are "integrated" shall mean that the parts or components are produced separately and subsequently joined together to produce a larger body. As used herein, the term "number" shall mean one or an integer greater than one (i.e., a plurality). As used herein, the word "unitary" means a component is created as a single piece or unit. That is, a component that includes pieces that are created separately and then coupled together as a unit is not a "unitary" component or body.

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

The present invention, as described in greater detail herein in connection with various particular exemplary embodiments, pertains to improvements in systems and methods for diagnosing, preventing, and treating OSA-related bruxism events in patients who use PAP therapies to treat OSA. While bruxism is often considered by dentists to be a singular disorder, it is considered to be both a neurological disorder and a compensation mechanism in sleep medicine. Consequently, dentists tend to approach bruxism from a treatment perspective, often recommending a dental device comprising a cap resting on the lower or upper teeth to protect the teeth from mechanical abrasion that results from nocturnal grinding of the teeth in order to treat the symptoms and eliminate the side effects of bruxism. In contrast, the present invention utilizes gear used for PAP therapy in the treatment of OSA to monitor metrics related to bruxism events in order to prevent subsequent bruxism events and/or stop a current bruxism event.

Imaging modalities and acoustical measurements obtained by techniques, such as pharyngometry and rhinometry, enable validation of airway patency and measurement of the cross-section of the upper airway during teeth grinding, and the present invention seeks to utilize these modalities and measurements to prevent and/or mitigate bruxism events by monitoring the physiological symptoms resulting from sympathetic activity associated with OSA. Acoustical rhinometry involves generating an acoustic pulse from a speaker and transmitting the sound pulse to the nasal cavity along a tube. The sound pulse is reflected back to a microphone, and the cross-sectional area of the nasal cavity can be determined by relating changes in the local acoustic impedance to cross-sectional area of the nasal cavity. Similarly, acoustical pharyngometry involves generating an acoustic pulse from a speaker and transmitting the sound pulse to the upper airway along a tube. The sound pulse is reflected back to a microphone, and the cross-sectional area of the upper airway can be determined by relating changes in the local acoustic impedance to cross-sectional area of the upper airway and defining cross-sectional area of the upper airway as a function of distance from the oral opening.

The ability to measure the effect of bruxism on the upper airway during sleep using PAP therapy gear in accordance with the systems and methods of the present invention leads to benefits such as: providing insights into the effect of bruxism on OSA and which therapy or combination of therapies is needed for a specific patient; establishing whether bruxism events have a positive or negative effect on airway patency, or alternatively adjusting PAP therapy settings to provide acceptable pressures during bruxism events or adjusting mandibular protrusion (either with an oral device or by a positional maneuver of the head or trunk); and identifying a more suitable teeth protection device which would not interfere with a potentially positive influence on airway patency. In one example, muscle tone increases during teeth grinding and the increased sympathetic activity also increases the tone in the upper airway (e.g. tongue base and palatal area), hence, less pressure would be needed during PAP therapy to gain airway patency. In another example, in a specific population afflicted with bruxism and OSA, when people in said population start to grind their teeth, the systems and methods of present invention would increase the PAP pressure so that less compensation by the body would occur, which is beneficial because it is believed that lesser compensation may reduce sympathetic activity, which in turn may stop teeth grinding.

Accordingly, the present invention pertains to a clinical decision support system 1 (described in more detail herein with respect to FIGS. 1 and 2) and a method 100 (described in more detail herein with respect to FIG. 3) that measures the upper airway cross-section before and during bruxism by pharyngometry or rhinometry in a PSG setting. Alternatively, an endoscopy camera measures the cross-section and visualizes the shape of the airway and type of airway collapse. System 1 also analyzes the flow pattern during inspiration to detect an onset of bruxism and to correlate a bruxism event with changes in flow pattern in a PSG setting. Based on the flow reduction in a hypopnea event, the system will predict a next bruxism event and will adapt the pressure in an auto-PAP (APAP) device to avoid or mitigate a coming bruxism event.

Figure 2:
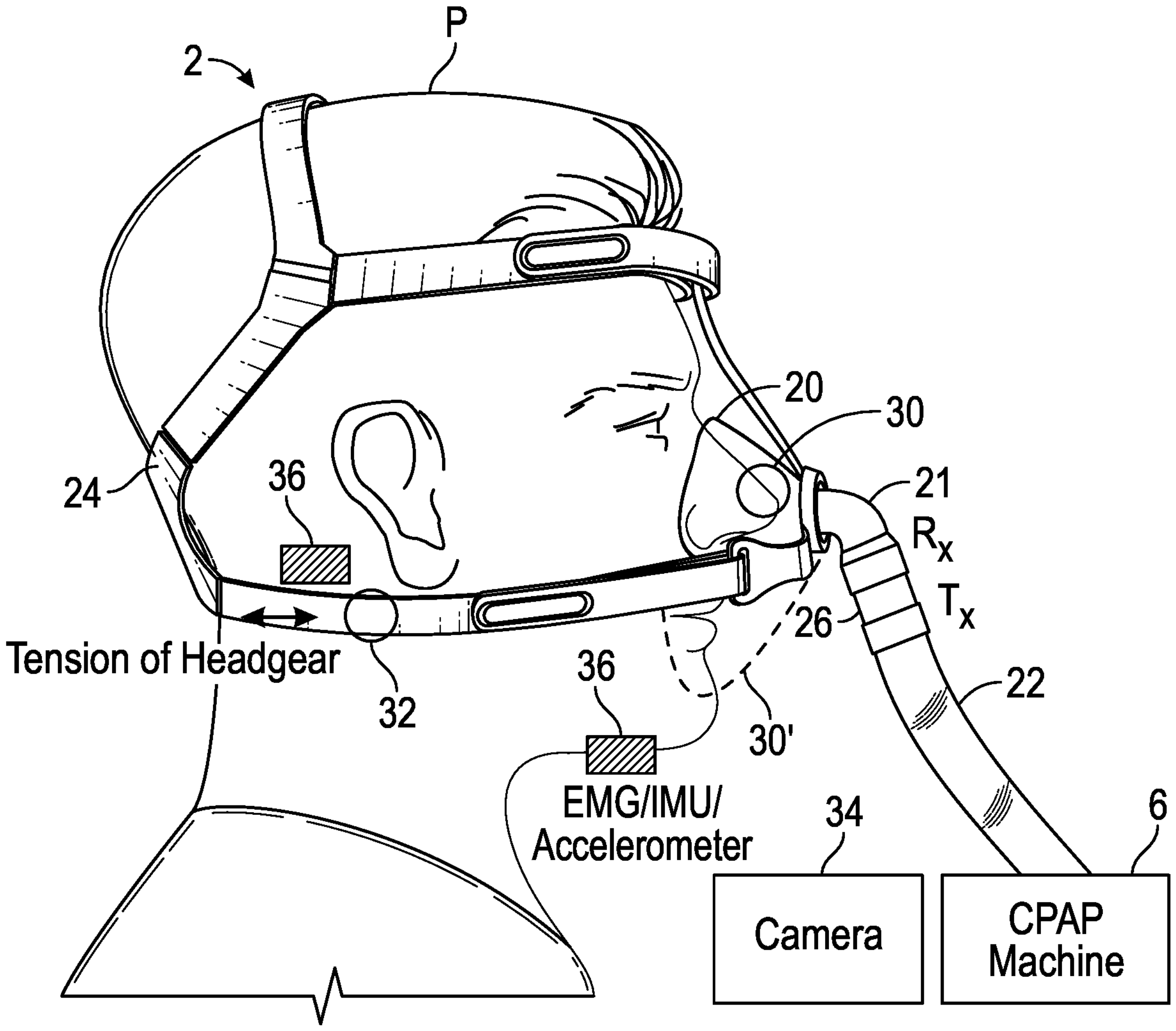
FIG. 2 shows positive airway pressure (PAP) equipment with various sensors integrated in order to detect physiological activity indicative of bruxism disposed on the face of a patient in accordance with an exemplary embodiment of the present invention.

Referring to FIG. 1, in an exemplary embodiment of the present invention, clinical decision support system 1 is used to detect or predict a bruxism event for a patient P and includes sensorized PAP equipment 2 comprising one or more sensors 3 either affixed to or integrated within PAP equipment 2 (PAP equipment 2 and sensors 3 being depicted more clearly and described in more detail with respect to FIG. 2). System 1 can be used either during PSG in a clinical setting or during PAP therapy self-administered by a patient at home. It will be appreciated that administration of PAP therapy to a patient generally requires that various combinations of a patient interface, mask, and/or headgear be coupled to the face and head of a patient. For brevity, the various gear and accessories necessary for delivering pressurized air during PAP therapy to a patient airway is simply referred to herein as “PAP equipment” 2, and it should be understood that PAP equipment 2 is intended to include an interface, mask, and/or headgear, and that alternative combinations of pressure support equipment appropriate for providing PAP therapy can be used without departing from the scope of the disclosed concept. A mandibular advancement device (MAD) 4 is also shown, as in an exemplary embodiment, patient P also uses a MAD.

PAP equipment 2 is operatively coupled to a PAP machine 6 comprising a controller 8 and a pressurized air generator 10. Controller 8 is in electrical communication with pressurized air generator 10 and is configured to enable a user to adjust the settings of the PAP therapy provided to patient P, to receive and transmit data from the sensors 3, and to automatically adjust the settings of the PAP therapy provided to patient P based on data received from the sensors 3, as explained in more detail herein with respect to method 100. While controller 8 is depicted as being part of the PAP machine 6, controller 8 can optionally instead be part of a remote platform (e.g., cloud engine or any other remote device) in electrical communication with pressurized air generator 10. System 1 further comprises a data server 12, which is a cloud server in an exemplary embodiment of the present invention. Controller 8 and data server 12 are in electrical communication with one another. In exemplary embodiments of the disclosed concept, data server 12 is additionally configured to communicate with a clinician dashboard 14 and a remote device 16.

Communications between data server 12 and clinician dashboard 14 enable a practitioner (including but not limited to, a sleep engineer, physician, and/or other clinicians monitoring the PAP treatment of patient P) to monitor bruxism and OSA activity and to adjust the PAP therapy settings of patient P. Remote device 16 is a personal communication device of patient P and can comprise, for example and without limitation, a mobile phone. Communications between data server 12 and remote device 16 enable alerts to be sent to patient P if action needs to be taken based on the data collected by the controller 8 from the sensors 3. In one non-limiting illustrative example, controller 8 can be programmed to send an alert to remote device 16 in order to advise patient P to see a dentist if tooth grinding has been detected by system 1 for a period of a two weeks and/or to advise patient P to see a sleep physician if the PAP device settings are insufficient to eliminate or lower the number of bruxism events during sleep. It will be appreciated that controller 8, data server 12, clinician dashboard 14, and remote device 16 can all be considered controllers, and as such, controller 8 may sometimes be referred to hereinafter as “treatment controller 8” in order to differentiate it from data server 12, clinician dashboard 14, and remote device 16.

Referring now to FIG. 2, PAP equipment 2 is shown in more detail. In the illustrative example shown in FIG. 2, PAP equipment 2 comprises a patient interface 20, a hose adapter 21, a conduit 22, and headgear 24. Interface 20 shown in FIG. 2 is a nasal mask style interface, but it should be understood that interface 20 can alternatively comprise nasal cushions, an oral mask (as depicted by the dashed line numbered 30'), or some combination of nasal and oral interfaces or cushions without departing from the scope of the disclosed concept. Hose adapter 21 additionally comprises an inductive coil 26 that can be used to power a microphone integrated into the interface 20 (explained in more detail herein below with respect to sensor 30) and to transmit and receive electrical signals between the microphone and controller 8. It will be appreciated that headgear 24 secures interface 20 to the face of patient P to create a seal in order to maintain the pressure of the pressurized air output by the PAP machine 6 through conduit 22 and hose adapter 21 and into the airway of patient P.

Three main categories of uses of the various sensors coupled to PAP equipment 2 are embodied in the present invention. In a first exemplary embodiment of the present invention, an acoustical rhinometer (which uses sound reflection to quickly assess the cross-sectional area of the upper airway) and/or an acoustical pharyngometer which uses sound reflection to quickly assess the cross-sectional area of the nasal cavity) are used to take measurements in order to determine airway patency. For acoustical rhinometry, a sensor 30 comprising a microphone and loudspeaker are integrated into either a nasal interface or nasal cushions. In the case of a nasal interface (such as interface 20 shown in FIG. 2), a microphone and loudspeaker 30 are integrated in the interface 20 via the hose adapter 22, while in the case of nasal cushions the microphone and loudspeaker 30 are integrated in a nostril tube adapter incorporated into the interface 20. For acoustical pharyngometry, a microphone and loudspeaker 30 are integrated into either the hose adapter 22 or an oral tube. In case of a mandibular advancement device (MAD), the patient wears a nasal mask. In an exemplary embodiment directed toward MAD treatment, a loudspeaker and microphone are integrated in the mask at the PAP hose adapter 21 to enable rhinometry. For pharyngometry with a MAD, a loudspeaker and microphone are integrated in a tube connected to the upper part of the MAD.

Still referring to FIG. 2, in a second exemplary embodiment, sound and/or vibration sensors are integrated in the headgear (as is the case with sensor 32) or mask (as is the case with sensor 30). These sound or vibration sensors can be regular microphones or wireless thin-film microphones (comprising printed electronics printed on headgear 24) that are inductively powered through coil 26 in the hose adapter 22. In this embodiment, the sensor 30 used for rhinometry and pharyngometry in the previously described embodiment and sensor 32 are used to sense and monitor acoustical signals generated by grinding of the teeth. Signal processing and filtering are needed to differentiate between bruxism sounds, the sound from the PAP machine 6, irregular bruxism sounds, and even snoring noises, and it will be appreciated that techniques such as Fast Fourier analysis, power spectral density, and/or other signal processing techniques suitable for this purpose can be employed by controller 8.

Still referring to FIG. 2, in a third exemplary embodiment, a camera 34 is used to sense masticatory muscle activity (MMA) and orofacial activity (OFA), and a processing unit (which can be incorporated, for example, in controller 8) analyzes the images to determine and distinguish between teeth grinding/bruxism and non-bruxism related muscle activity. In this embodiment, camera 34 can either be used to complement either of the first two embodiments (the first embodiment being that in which the sensor 30 is used for rhinometry and/or pharyngometry, the second embodiment being that in which sensor 32 is used to monitor teeth grinding), or camera 34 can be used alone without the use of microphones. In one non-limiting example, camera 34 can comprise an endoscopy camera.

Figure 3:
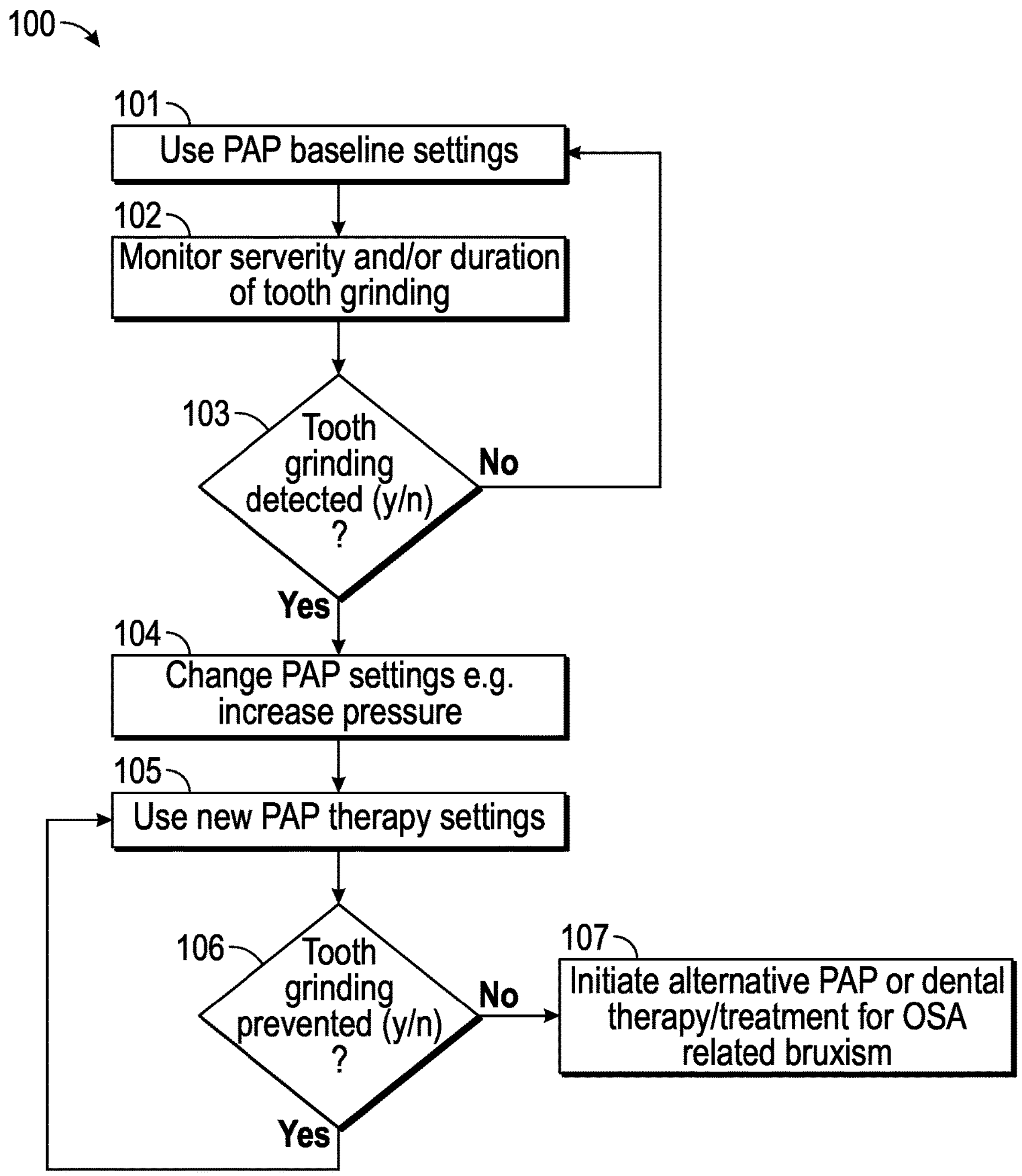
FIG. 3 is a flow chart of a method used to diagnose OSA-related bruxism and to adjust therapy/treatment settings for PAP therapy using the support system shown in FIG. 1 and the PAP equipment shown in FIG. 2, in accordance with an exemplary embodiment of the present invention.

In addition, EMG sensors, inertial measurement units (IMU), and/or accelerometers can be placed at the chinbone or masticatory muscles to monitor MMA in this embodiment, in the approximate locations where sensors 36 are positioned in FIG. 3. This embodiment constitutes an improvement in the field, as currently, there are no means to measure the impact on the cross-section and the pressure related modulation of the airway patency during the respiration cycle. It is known to measure MMA with superficial EMG sensors during a PSG; however, superficial EMG activity is insufficient to distinguish between MMA activity and other muscles activity (OMA). Hence, complementing superficial EMG (or IMU or accelerometer) monitoring with OFA monitoring by camera 34 enables differentiation between MMA and OMA.

FIG. 3 is a flow chart of a method 100 executed by controller 8 of system 1 in order to detect, monitor, and/or predict the onset of bruxism events and to adapt PAP therapy settings of the PAP machine 6 in order to avoid subsequent bruxism events or stop a current bruxism event. At step 101, PAP machine 6 operates using set of baseline PAP settings to output pressurized air to the airway of patient P. At step 102, the severity and/or duration of tooth grinding is monitored based on the measured bruxism-related physiological signals previously described with respect to FIG. 2. If tooth grinding is not detected at decision point 103, the method returns to step 101 so that PAP machine 6 can continue operating using the same baseline PAP settings. If tooth grinding is detected at decision point 103, controller 8 adjusts the PAP settings at step 104. One non-limiting example of a change to PAP settings that can be made at step 104 is an increase in the pressure of the pressurized air output by PAP machine 6.

After PAP settings are adjusted at step 104 and PAP machine 6 operates using the adjusted PAP settings at step 105, the efficacy of the adjusted PAP settings is evaluated at decision point 106. If controller 8 determines, based on the measured bruxism-related physiological signals, that tooth grinding has been prevented by the new PAP settings implemented at step 105, then method 100 returns to step 105 to continue using the adjusted PAP settings. If controller 8 determines that tooth grinding has not been prevented, controller 8 then issues an alert at step 107 that alternative PAP, other OSA modalities, or dental therapy/treatment/modalities for OSA-related bruxism should be implemented (such alert being communicated to server 12 such that dashboard 14 and/or remote device 16 can access or receive the alert). In an exemplary embodiment, controller 8 additionally automatically initiates scheduling of an appointment with a dentist or other clinician when issuing an alert at step 107.

In an alternative exemplary embodiment, patient P may be using a MAD 4 as shown in FIG. 1, and controller 8 will check inspiratory flow instead of teeth grinding at decision points 103 and 106, and adjust the settings of the MAD 4 at step 104 in order to adjust the mandibular protrusion at step 104 if the inspiratory flow is found to be unsatisfactory, and operate using the adjusted MAD settings at step 105. In another exemplary embodiment, if controller 8 determines that tooth grinding has not been prevented, appointments with dental or sleep professionals can be initiated automatically through a connected platform in order to find alternative bruxism or OSA treatment/therapy options for patient P. Such alternative treatment/therapy options may include, for example and without limitation, a nightguard, a MAD (in the case where a MAD is not already being used), or a positional therapy device.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. Positive airway pressure therapy (PAP) equipment for recognizing and ameliorating sleep bruxism events in a patient during therapy for obstructive sleep apnea (OSA), the PAP equipment comprising:
- a patient interface structured to be coupled to an airway of the patient;
- headgear coupled to the patient interface and structured to secure the patient interface to a head of the patient;
- at least one sensor integrated into the patient interface and/or the headgear; and
- a controller electrically and operatively coupled to the that least one sensors and configured to be electrically and operatively coupled to a positive pressure generator that generates a flow of breathing gas,
- wherein the at least one sensor is configured to detect physiological signals related to bruxism events, and
- wherein the controller is configured to decide whether to change an output of the positive pressure generator or propose alternative OSA or dental treatment modalities based on the signals detected by the at least one sensor;
- a hose coupled at a first end to the patient interface and structured to be coupled at a second end to the positive pressure generator, wherein the patient interface comprises an integrated microphone in electrical communication with the controller as the at least one sensor,
- wherein the integrated microphone is configured to sense acoustical signals generated by teeth grinding, and
- wherein the controller is configured to perform signal processing and filtering to differentiate between teeth grinding acoustical signals and other acoustical signals, and
- wherein the controller is configured to provide breathing gas at a first baseline continuous positive pressure and to increase the baseline continuous positive pressure in response to the signals detected by the at least one sensor being indicative of teeth grinding and in the absence of a concurrent apnea event being experienced by the patient.

2. The PAP equipment of claim 1, wherein the patient interface comprises a nasal interface, wherein the at least one sensor comprises a loudspeaker configured to project an acoustical signal into a nasal cavity of the patient and a microphone configured to receive the acoustical signal after the acoustical signal has been reflected from the nasal cavity of the patient, wherein the controller is configured to determine a cross-sectional area of the nasal cavity by performing acoustical rhinometry, and wherein the controller is configured to recommend a change to settings of the positive pressure generator based on the acoustical rhinometry.

3. The PAP equipment of claim 1, wherein the patient interface comprises an oral interface, wherein the at least one sensor comprises a loudspeaker configured to project an acoustical signal into an oral cavity of the patient and a microphone configured to receive the acoustical signal after the acoustical signal has been reflected from the airway of the patient, wherein the controller is configured to determine a cross-sectional area of the airway by performing acoustical pharyngometry, and wherein the controller is configured to recommend a change to settings of the pressurized air generator based on the acoustical pharyngometry.

4. A positive airway pressure therapy (PAP) system for recognizing and stopping sleep bruxism events in a patient during therapy for obstructive sleep apnea (OSA), the system comprising:
- a positive pressure generator adapted to generate a flow of gas at a first baseline continuous positive pressure;
- a patient interface structured to be coupled to an airway of the patient;
- a conduit coupled at a first end to an output of the pressurized air generator and coupled at a second end opposite the first end to the patient interface;
- headgear coupled to the patient interface and structured to secure the patient interface to a head of the patient;
- at least one sensor integrated into the patient interface and the headgear; and
- a treatment controller electrically and operatively coupled to the at least one sensor and to the positive pressure generator, and configured to electrically communicate with external controllers;
- wherein the at least one sensor is configured to detect physiological signals related to bruxism events, and
- wherein the treatment controller is configured to decide whether to change increase the baseline continuous positive pressure provided by the positive pressure responsive to bruxism being detected and in the absence of a concurrent apnea event being experienced by the patient.

5. The PAP system of claim 4, wherein the patient interface comprises a nasal interface, wherein the at least one sensor comprises a loudspeaker configured to project an acoustical signal into a nasal cavity of the patient and a microphone configured to receive the acoustical signal after the acoustical signal has been reflected from the nasal cavity of the patient, wherein the treatment controller is configured to determine a cross-sectional area of the nasal cavity by performing acoustical rhinometry, and wherein the treatment controller is configured to recommend a change to settings of the pressurized air generator based on the acoustical rhinometry.

6. The PAP system of claim 4, wherein the patient interface comprises an oral interface, wherein at least one sensor comprises a loudspeaker configured to project an acoustical signal into an oral cavity of the patient and a microphone configured to receive the acoustical signal after the acoustical signal has been reflected from the airway of the patient, wherein the treatment controller is configured to determine a cross-sectional area of the airway by performing acoustical pharyngometry, and wherein the treatment controller is configured to recommend a change to settings of the pressurized air generator based on the acoustical pharyngometry.

7. The PAP system of claim 4, further comprising: a hose adapter coupled at a first end to the patient interface and coupled at a second end to the pressurized air generator, wherein the patient interface comprises an integrated microphone in electrical communication with the treatment controller as the at least one sensor, wherein the hose adapter comprises an inductive coil configured to power the microphone, wherein the integrated microphone is configured to sense acoustical signals generated by teeth grinding, and wherein the treatment controller is configured to perform signal processing and filtering to differentiate between teeth grinding acoustical signals and other acoustical signals.

8. The PAP system of claim 4, wherein the treatment controller is configured to increase pressure of air output by the pressurized air generator in response to the signals detected by at least one sensor being indicative of teeth grinding.

9. A method for recognizing and/or stopping sleep bruxism events in a patient during positive airway pressure (PAP) therapy for obstructive sleep apnea (OSA), the method comprising:

coupling a patient interface integrated with at least one sensor to an airway of the patient;

electrically and operatively coupling a controller to the at least one sensor and electrically and operatively coupling the treatment controller to a positive pressure generator;

configuring the at least one sensor to detect physiological signals related to bruxism events;

delivering a flow of gas to the patient at a first baseline continuous positive pressure; and causing the controller to increase the baseline continuous positive pressure provided by the positive pressure generator based on the signals detected by at least one sensor.

10. The method of claim 9, wherein the patient interface comprises a nasal interface, wherein at least one sensor comprises a loudspeaker configured to project an acoustical signal into a nasal cavity of the patient and a microphone configured to receive the acoustical signal after the acoustical signal has been reflected from the nasal cavity of the patient, wherein the method further comprises configuring controller to determine a cross-sectional area of the nasal cavity by performing acoustical rhinometry, and wherein the controller is configured to recommend a change to settings of the pressurized air generator based on the acoustical rhinometry.

11. The method of claim 9, wherein the patient interface comprises an oral interface, wherein the at least one sensor comprises a loudspeaker configured to project an acoustical signal into an oral cavity of the patient and a microphone configured to receive the acoustical signal after the acoustical signal has been reflected from the airway of the patient, wherein the controller is configured to determine a cross-sectional area of the airway by performing acoustical pharyngometry, and wherein the controller is configured to recommend a change to settings of the pressurized air generator based on the acoustical pharyngometry.

12. The method of claim 9, further comprising:

coupling a first end of a hose adapter to the patient interface and a second end disposed opposite the first end to the pressurized air generator;

configuring the controller to perform signal processing and filtering to differentiate between teeth grinding acoustical signals and other acoustical signals, wherein the patient interface comprises an integrated microphone in electrical communication with the controller, wherein the hose adapter comprises an inductive coil configured to power the microphone, and wherein the integrated microphone is configured to sense acoustical signals generated by teeth grinding.

13. The method of claim 9, further comprising: configuring the treatment controller to increase pressure of air output by the pressurized air generator in response to the at least one sensor detecting teeth grinding.

* * * * *